(12) United States Patent
Kojima et al.

(10) Patent No.: US 8,087,515 B2
(45) Date of Patent: Jan. 3, 2012

(54) SEPARATION METHOD AND SEPARATION APPARATUS (75) Inventors: Hiroshi Kojima, Kanagawa (JP); Kazuya Hongo, Kanagawa (JP); Seiichi Takagi, Kanagawa (JP); Tetsuo Ohta, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 83 days.

(21) Appl. No.: 12/397,714

(22) Filed: Mar. 4, 2009

(65) Prior Publication Data

US 2010/0072112 A1 Mar. 25, 2010

(30) Foreign Application Priority Data

Sep. 25, 2008 (JP) ................. 2008-245741

(51) Int. Cl.
*B03B 5/00* (2006.01)
(52) U.S. Cl. ....... 209/155; 209/18; 209/172.5; 209/208; 209/422
(58) Field of Classification Search .............. 209/18, 209/39, 40, 172.5, 155, 208, 422
See application file for complete search history.

(56) References Cited

U.S. PATENT DOCUMENTS

| 6,454,945 | B1* | 9/2002 | Weigl et al. ............. 210/634 |
| 7,328,807 | B2 | 2/2008 | Takagi et al. |
| 7,550,267 | B2* | 6/2009 | Hawkins et al. ............. 435/7.1 |
| 7,572,375 | B2* | 8/2009 | Takagi et al. ............. 210/634 |
| 7,732,725 | B2* | 6/2010 | Takagi et al. ............. 209/131 |
| 2002/0108889 | A1* | 8/2002 | Fujii et al. ............. 209/39 |
| 2006/0169589 | A1* | 8/2006 | Takagi et al. ............. 204/515 |
| 2007/0007220 | A1* | 1/2007 | Takagi et al. ............. 210/800 |
| 2007/0119754 | A1* | 5/2007 | Takagi et al. ............. 209/127.1 |
| 2008/0017553 | A1* | 1/2008 | Takagi et al. ............. 209/172.5 |
| 2009/0117664 | A1* | 5/2009 | Shinoda ............. 436/172 |
| 2010/0072112 | A1* | 3/2010 | Kojima et al. ............. 209/39 |

FOREIGN PATENT DOCUMENTS

| JP | B-35-012045 | 8/1960 |
| JP | A-11-508182 | 7/1999 |
| JP | A-2000-512898 | 10/2000 |
| JP | A-2003-251336 | 9/2003 |
| JP | A-2006-116520 | 5/2006 |
| JP | A-2006-187770 | 7/2006 |
| JP | A-2007-175684 | 7/2007 |
| WO | WO 97/00442 | 1/1997 |
| WO | WO97/48493 A1 | 12/1997 |

OTHER PUBLICATIONS

Oct. 12, 2010 Japanese Office Action issued in Japanese Patent Application No. 2008-245741 (with translation).

* cited by examiner

*Primary Examiner* — Terrell Matthews
(74) *Attorney, Agent, or Firm* — Oliff & Berridge, PLC (57) ABSTRACT

A separation apparatus contains: a dispersion liquid introduction path to which a dispersion liquid containing particles is introduced; a separation path that has a inclined upper face inclined with respect to a direction of gravity and separates the particles; and a discharge path from which particles separated by the separation path are discharged.

17 Claims, 9 Drawing Sheets

DIRECTION OF GRAVITATIONAL FORCE

PARTICLE SIZE DISTRIBUTION

SEPARATION METHOD AND SEPARATION APPARATUS

CROSS-REFERENCE TO RELATED APPLICATIONS

This application is based on and claims priority under 35 U.S.C. 119 from Japanese Patent Application No. 2008-245741 filed Sep. 25, 2008.

BACKGROUND

1. Technical Field

The present invention relates to a separation method and a separation apparatus.

2. Related Art

Dry methods and wet methods are available as methods for classifying and/or separating particles. In dry methods, since the difference in specific gravity between a liquid and particles becomes large, high accuracy is obtained in some methods. In wet methods, although the difference in specific gravity between a liquid and particles becomes small, since the particles are dispersed easily in the liquid, high classification accuracy is obtained for fine powder. A classification apparatus usually comprises a rotor serving as a rotating portion and a stator serving as a stationary portion and performs classification on the basis of the balance between the centrifugal force and the inertia of particles. In addition, a classifier using the "Coanda effect" and having no rotating portion is commercially available as a classifier for performing a dry method. On the other hand, in recent years, various methods for performing chemical reactions and unit operations in the micro field have been studied, and the development of methods and apparatuses for efficiently classifying particles without causing contamination or the like have been examined.

SUMMARY

According to an aspect of the present invention, there is provided a separation apparatus containing: a separation path that has a inclined upper face inclined with respect to a direction of gravity and separates particles contained in a dispersion liquid; a dispersion liquid introduction path that introduces the dispersion liquid into the separation path; and a discharge path that discharges particles separated by the separation path from the separation path.

BRIEF DESCRIPTION OF THE DRAWINGS

Exemplary embodiment of the present invention will be described in detail based on the following figures, wherein.

DETAILED DESCRIPTION

The separation apparatus according to the exemplary embodiment of the present invention has a dispersion liquid introduction path that introduces a dispersion liquid containing particles, a separation path that separates the particles, and a discharge path that discharges the separated particles, wherein the upper face of the separation path is inclined with respect to the direction of gravity.

Furthermore, the separation method according to the exemplary embodiment of the present invention comprises a dispersion liquid introducing step of introducing a dispersion liquid containing particles into the dispersion liquid introduction path, a separating step of separating the particles by passing the dispersion liquid through the separation path, the upper face of which is inclined with respect to the direction of gravity, and a discharging step of discharging the separated fractions of the particles from the discharge paths.

The direction of gravity is herein synonymous with the downward vertical direction.

In the case of separating particles on the order of micrometers or classifying particles on the order of micrometers using a force other than diffusion, particles can be moved forcibly. It is thus not always necessary to use a long path. However, it is necessary to release the external force other than diffusion once or to control the external force to avoid clogging of the path.

In the present invention, "separation" is not limited to the case in which particles in a dispersion liquid are separated from the dispersion liquid without being classified, but includes a mode in which the particles contained in the dispersion liquid are classified and separated. In other words, it is also possible to say that the separation apparatus according to the exemplary embodiment of the present invention is a classification apparatus and/or a separation apparatus, and that the separation method according to the exemplary embodiment of the present invention is a classification method and/or a separation method.

In the following description of the exemplary embodiment of the present invention, the dispersion medium of a dispersion liquid containing particles is also simply referred to as a dispersion medium.

(Separation Path)

The separation apparatus according to the exemplary embodiment of the present invention is provided so that the upper face of the separation path is inclined with respect to the direction of gravity (in the vertical direction). Furthermore, the separation method according to the exemplary embodiment of the present invention has a separating step of separating particles contained in a dispersion liquid by passing the dispersion liquid through the separation path, the upper face of the separation path is inclined with respect to the direction of gravity.

In the case that the specific gravity of the particles is smaller than that of the dispersion medium of the dispersion liquid containing the particles, the particles float depending on the diameter of the particles. Particles having large diameters rise rapidly and collide with the upper face of the separation path. The flow velocity of the fluid under laminar flow conditions becomes the velocity of a Poiseuille flow. Since the flow velocity at the center of the path is maximal and the velocity near the wall face of the path is nearly zero, the particles collided with the upper face of the path rise along the slope of the upper face by virtue of a buoyant force and are discharged from the discharge path disposed in the upper portion of the separation path. In the case that the dispersion liquid is fed from upward to downward, particles having small diameters are discharged from the discharge path disposed in the lower portion of the separation path without colliding with the slope. In the exemplary embodiment of the present invention, at least one discharge path should only be provided. A particle reservoir may also be used instead of the discharge path provided in the upper portion of the discharge path.

In the exemplary embodiment of the present invention, the inclination angle of the upper face of the separation path may be selected appropriately from among angles larger than 0°, and the angle is preferably about 15' or larger than or equal to 15° from the viewpoint that particles float (rise) along the slope. In addition, the inclination angle is preferably about 75° or smaller than or equal to 75° from the viewpoint of obtaining sufficient separation efficiency. The inclination angle of the separation path is more preferably from 20° or about 20° to 70° or about 70°, and further more preferably from 30° or about 30° to 60° or about 60°.

The inclination angle of the separation path is the inclination angle of the upper face of the separation path with respect to the direction of gravity. For example, the inclination angle of a horizontal path is 0°. The inclination angle of the bottom face of the separation path is not limited particularly in the present embodiment.

In the exemplary embodiment of the present invention, it is preferable that the separation path is a microchannel. In the case that the separation path is a microchannel, the floating distance of particles becomes short, the time until particles make contact with the inclined wall of the upper face decreases, and the efficiency increases. Furthermore, the laminar flow may be maintained even in the case that the flow velocity is high, whereby reduction in separation capability due to turbulent flow may be prevented. Moreover, the velocity of particles at the wall face of the separation path under laminar flow conditions is nearly zero, whereby the configuration in which the separation path is a microchannel is preferable since the separation efficiency of the separation apparatus is improved.

Paths having a width of several micrometers to several tens of millimeters are preferably used as microchannels. The separation apparatus according to the exemplary embodiment of the present invention may be a separation apparatus having multiple separation paths.

The circle-equivalent diameter of the separation path is preferably from 10 μm or about 10 μm to 10 mm or about 10 mm, more preferably from 500 μm or about 500 μm to 5 mm or about 5 mm. In the case that the diameter of the separation path is within the above-mentioned range, occurrence of turbulent flow is prevented, and the floating distance of particles is short, whereby this configuration is preferable since the separation efficiency is improved. Furthermore, this configuration is preferable since clogging of the path due to particles is suppressed.

A microchannel is defined as a path in which the dimension (typical length) thereof is small, the flow velocity of a fluid flowing therethrough is small, and the Reynolds number of the flow is 2,300 or less. Hence, a separation apparatus having a microchannel is an apparatus in which laminar flow is dominant, thereby being different from ordinary apparatuses in which turbulent flow is dominant.

The Reynolds number (Re) is herein obtained as described below, and laminar flow becomes dominant when the Reynolds number is 2,300 or less.

The Reynolds number (Re) is proportional to the flow velocity (u (m/s)) and the typical length (L (m)).

$$R_e = \frac{uL}{v} \quad (1)$$

where v is the kinematic viscosity coefficient (m$^2$/s) of the fluid.

The typical length (L (m)) is given by the following expression (2) in the case that the path has a rectangular cross-section.

$$L = \frac{4S}{l_p} \quad (2)$$

where S is the cross-sectional area (m$^2$) of the path, and lp is the circumferential length (m) of the path.

When it is assumed that the width of the rectangular cross-section is x (m) and the height thereof is t (m), the following expression (3) is established.

$$S = tx \; l_p = 2(x+t) \quad (3)$$

When it is assumed that the flow rate of the fluid is a (m$^3$/s), the following expression (4) is established.

$$u = \frac{a}{S} \quad (4)$$

When Expressions (2), (3) and (4) are substituted into Expression (1), the following expression (5) is derived.

$$Re = \frac{2a}{v} \cdot \frac{1}{x+t} \quad (5)$$

A case in which pure water is fed through a rectangular path at a constant flow velocity (for example, 10 ml/h) is herein taken as an example and considered. The kinematic viscosity coefficient v of the pure water is 0.893×10$^{-7}$ m$^2$/s at 25° C.

When it is assumed that the height t of the path is constant and that the width x of the path is a variable, the Reynolds number is inversely proportional to the width of the path.

In this way, it is possible to design a path wherein the Reynolds number is 2,300 or less. In the case that the height t is sufficiently small, laminar flow may be maintained even if the width x of the path is large.

The separation principle of the separation apparatus according to the exemplary embodiment of the present invention will be described below.

(Separation Principle)

In the exemplary embodiment of the present invention, particles influenced by a buoyant force in the dispersion liquid will float upward relative to the direction of gravity (upward in the vertical direction). The particles significantly influenced by the buoyant force are collected using the discharge path provided in the upper portion of the separation path. On the other hand, as the dispersion liquid and/or transport liquid is fed, particles slightly influenced by the buoyant force are fed to the downstream and discharged from the discharge path provided in the lower portion of the separation path. The floating velocity of the floating particles is raised by providing an inclination to the upper face of the separation path, whereby the efficiency is improved.

In the separation apparatus and the separation method according to the exemplary embodiment of the present invention, the particles contained in the dispersion liquid may be classified using the separation path (preferably, a microchannel) and using the difference in the floating velocities of the particles or may be separated (collected) without performing classification.

The separation apparatus according to the exemplary embodiment of the present invention includes the dispersion liquid introduction path, the separation path and the discharge paths, and also has a transport liquid introduction path as necessary. In the exemplary embodiment of the present invention, it is preferable that liquid feeding in all the paths is performed under laminar flow conditions.

In the exemplary embodiment of the present invention, since the upper face of the separation path is inclined, the particles having floated and made contact with the slope further float upward along the upper face of the separation path, that is, the inclined wall face. Since the flow velocity at the wall face is nearly zero under laminar flow conditions as described above, the particles having made contact with the upper face of the separation path are hardly influenced by a downstream flow even if such a downstream flow is present, and the particles float. Hence, the separation apparatus according to the exemplary embodiment of the present invention may separate particles using a short path length in a short time in Comparative with the conventional floatation-type separation apparatuses.

In the case that the specific gravity of particles is smaller than that of the dispersion medium of the dispersion liquid, the particles float. The floating velocity of the particles at the floating time is different depending on the specific gravity or the diameter of the particles. In the case that the separation apparatus according to the exemplary embodiment of the present invention is used as a classification apparatus, particles are classified using the difference in the floating velocity. In the case that there is a difference in particle diameter, the floating velocity is proportional to the square of the particle diameter. The larger the particle diameter, the faster the particles float (according to Stokes equation).

In the exemplary embodiment of the present invention, the range of particles to which this classification method is applicable may be extended by exerting an external force being proportional to the diameter of the particles instead of using the difference in floating velocity. A force exerted by an electric or magnetic field is taken as an example of the external force.

Even in the case that the specific gravity of particles is larger than that of the dispersion medium, the separation apparatus according to the exemplary embodiment of the present invention is applicable by adsorbing minute bubbles having a diameter of several nanometers to several hundred micrometers and referred to as microbubbles and/or nanobubbles to the particles under specific conditions.

When the particles having floated as described above make contact with the upper face of the separation path, the particles float along the inclination of the upper face. Hence, the separation velocity of the particles is higher than that in the case that the upper face has no inclination.

(Particles)

In the exemplary embodiment of the present invention, although the size of particles to be separated is not limited particularly, it is preferable that the particle diameter (the diameter or the maximum diameter) of the particles is 0.1 µm or more and 1,000 µm or less. The separation apparatus and the separation method according to the exemplary embodiment of the present invention are more preferably applicable to the separation of particles having a particle diameter of 1 µm or more and 500 µm or less, and further more preferably applicable to the separation of particles having a particle diameter of 5 µm or more and 100 µm or less.

It is preferable that the particle diameter of particles is 1,000 µm or less since clogging of the path may be suppressed from occurring in this case. On the other hand, it is preferable that the particle diameter of particles is 0.1 µm or more since a floating velocity higher than that of Brownian motion is obtained in this case.

Types of particles to be separated are not limited particularly. Examples of the particles include resin particles, inorganic particles, metal particles, ceramic particles, cells (for example, lymphocytes, leucocytes and erythrocytes), not being limited particularly. In addition, it is also possible to use a biological sample (whole blood) or a solution obtained by appropriately diluting this sample as a dispersion liquid.

Furthermore, the separation apparatus may also separate polymer particles; organic crystals or aggregates, such as pigments; inorganic crystals or aggregates; particles of metal compounds, such as metal oxides and metal nitrides; toner particles; etc.

In particular, particles having a true specific gravity smaller that the specific gravity of the dispersion medium are preferable regardless of the presence or absence of voids inside the particles. In this case, examples of the particles include rubber particles, wax particles (minute particles of wax), hollow particles, etc.

Furthermore, the shape of particles is not limited particularly and may be spherical, spheroidal, amorphous or acicular. Among these shapes, spherical and/or spheroidal shapes are preferable since clogging of the path hardly occurs. The ratio of the major axis length and minor axis length (major axis length/minor axis length) is preferably 1 or more and 50 or less, more preferably 1 or more and 20 or less.

Specifically speaking, examples of the above-mentioned high polymer particles include particles of polyvinyl butyral resin, polyvinyl acetal resin, polyarylate resin, polycarbonate resin, polyester resin, phenoxy resin, polyvinyl chloride resin, polyvinylidene chloride resin, polyvinyl acetate resin, polystyrene resin, acrylic resin, methacrylic resin, styrene-acrylic resin, styrene-methacrylic resin, polyacrylamide resin, polyamide resin, polyvinyl pyridine resin, cellulosic resin, polyurethane resin, epoxy resin, silicon resin, polyvinyl alcohol resin, casein, vinyl chloride-vinyl acetate copolymer, modified vinyl chloride-vinyl acetate copolymer, vinyl chloride-vinyl acetate-maleic anhydride copolymer, styrene-butadiene copolymer, vinylidene chloride-acrylonitrile copolymer, styrene-alkyd resin, and phenol-formaldehyde resin.

Furthermore, examples of particles of the above-mentioned metals or metal compounds include particles of metals, such as carbon black, zinc, aluminum, copper, iron, nickel, chromium and titanium, or their alloys; metal oxides, such as $TiO_2$, $SnO_2$, $Sb_2O_3$, $In_2O_3$, ZnO, MgO and iron oxides, and their compounds; and metal nitrides, such as silicon nitride; and their combinations.

Pulverized particles of nitrile rubber, styrene rubber, isobutylene rubber, etc. may be used as the above-mentioned rubber particles. Emulsion polymerization and mechanical microparticulation, such as freezing/refrigerating pulverization, may be carried out for microparticulation.

Particles obtained by microparticulating resin according to either one of the methods using emulsion/dispersion apparatuses, described in "Emulsion/dispersion Technology and Particle Diameter Control of Polymer Particles, Chapter 3" Reaction Engineering Research Society Report 1, issued by Society of Polymer Science, Japan in March, 1955, can be used as the above-mentioned wax particles.

Furthermore, as the above-mentioned wax particles, it is possible to use wax particles (mold-releasing agent) obtained using a method in which a mold-releasing agent is added to an appropriate solvent that is compatible with the mold-releasing agent during warming and does not allow the mold-releasing agent to be dissolved at room temperature, the mold-releasing agent is dissolved under heating, and the mixture is gradually cooled to room temperature to allow the particles of the mold-releasing agent to be deposited (the dissolution-deposition method) or using a method in which a mold-releasing agent is evaporated under heating in an inert gas, such as helium, to produce particles in the gas phase, and the particles are cooled and collected by allowing them to attach to a film or the like and then dispersed into a solvent (the gas-phase evaporation method).

In the production of the above-mentioned wax particles, further microparticulation may be attained when the above-mentioned method is combined with a mechanical pulverization method in which a medium or the like is used.

Examples of resin serving as the material of the above-mentioned wax particles include low-molecular-weight polypropylene, low-molecular-weight polyethylene, etc. and waxes, i.e., plant-based waxes, such as carnauba wax, cotton wax, wood wax and rice wax, animal-based waxes, such as yellow beeswax and lanolin, mineral-based waxes, such as ozokerite and selsyn, and petroleum waxes, such as paraffin, microcrystalline and petrolactam. In addition to these natural waxes, synthetic hydrocarbon waxes, such as Fischer-Tropsch wax, are also included. Among these waxes, low-molecular-weight polypropylene, low-molecular-weight polyethylene, carnauba wax and paraffin are used preferably as resin serving as the material of the above-mentioned wax particles.

Inorganic/organic hollow particles may be used as the above-mentioned hollow particles. Silica-based and silica-alumina-based hollow particles are preferably used as inorganic hollow particles, and resin-based hollow particles are preferably used as inorganic hollow particles. Furthermore, the number of voids inside a particle may be singular or multiple. The porosity thereof, not limited particularly, is preferably 20 to 80%, more preferably 30 to 70%. More specifically, examples of the hollow particles include inorganic hollow particles, such as Fillite produced by Japan Fillite Co., Ltd. and Cenolite produced by TOMOE Engineering Co., Ltd., and organic hollow particles, such as Expancel produced by Japan Fillite Co., Ltd., ADVAN CELL produced by Sekisui Chemical Co., Ltd., SX866(A) and SX866(B) produced by JSR Corporation and Nipol MH5055 produced by Nippon Zeon Co., Ltd. Among these, Expancel of Japan Fillite Co., Ltd. is preferably used as the above-mentioned hollow particles. In particular, thermally expandable particles, such as Expancel DU, are expanded to a desired size by appropriate heating before use.

These particles are produced using various production methods and, in many cases, produced inside a medium liquid (dispersion medium) by synthesis and then just separated. However, there is a case in which particles produced by mechanically cracking block objects are dispersed into a medium liquid and then separated. In this case, cracking is frequently performed in the medium liquid (dispersion medium), and in the case, cracked particles are just separated.

On the other hand, in the case that powder (particles) produced by a dry method is separated, the powder is required to be dispersed preliminarily in a medium liquid. Examples of methods for dispersing dry powder into a medium liquid include methods that use machines, such as a sand mill, a colloid mill, an attritor, a bowl mill, a Dinomill, a high-pressure homogenizer, an ultrasonic disperser, a Coball Mill and a roll mill. However, at the time of dispersion, it is preferable that the dispersion is carried out under the conditions that primary particles are not pulverized by the dispersion.

(Dispersion Medium and Transport Liquid)

Any solvents, not limited particularly, may be used as the dispersion medium and transport liquid of a dispersion liquid containing particles. However, it is preferable to use a solvent having a specific gravity larger than that of at least one kind of particles inside the dispersion liquid. It is also preferable to use a solvent having a specific gravity larger than those of all the kinds of particles inside the dispersion liquid. The transport liquid is defined as a solvent not containing particles and fed to the separation path.

In the case that the specific gravities of the dispersion medium and the transport liquid are larger (heavier) than that of particles, it is preferable that the difference obtained by subtracting the specific gravity of the particles from the specific gravity of the dispersion medium or the transport liquid is 0.01 or more. Although it is preferable that the difference in specific gravity is larger to obtain higher floating velocity of the particles, the difference is preferably 20 or less. The difference in specific gravity is more preferably from 0.05 to 11, further more preferably from 0.05 to 4. In the case that the difference obtained by subtracting the specific gravity of the particles from the specific gravity of the dispersion medium or the transport liquid is 0.01 or more, the difference is preferable since the particles float. On the other hand, in the case that the difference is 20 or less, the difference is preferable since the floating speed of the particles is appropriate and clogging hardly occurs.

The dispersion medium and the transport liquid may be the same or different from each other.

If the difference obtained by subtracting the specific gravity of the particles from the specific gravity of the dispersion medium is 0.01 to 20 as in the case described above, the dispersion medium may be used preferably as a dispersion medium or a transport liquid for the exemplary embodiment of the present invention. Examples thereof include water, a water-based medium and an organic solvent medium.

Examples of the above-mentioned water include ion-exchanged water, distilled water and electrolytic ionized water. In addition, specifically speaking, examples of the above-mentioned organic solvent medium include methanol, ethanol, n-propanol, n-butanol, benzyl alcohol, glycerin, methyl cellusolve, ethyl cellusolve, acetone, methyl ethyl ketone, cyclohexane, methyl acetate, n-butyl acetate, dioxane, tetrahydrofuran, methylene chloride, chloroform, chlorobenzene, toluene, xylene and a mixture of two or more kinds of these.

The dispersion medium and transport liquid preferably used in the exemplary embodiment of the present invention are different depending on the kind of particles to be separated. Examples of a preferred combination of particles and a dispersion medium include a combination of polyolefin particles or hollow particles and ion-exchanged water. Among these combinations, a combination of paraffin wax particles, carnauba wax particles or thermally expandable Expancel particles and ion-exchanged water is preferable.

In the case that bubbles are attached to particles or that particles are floated by exerting an external force, such as a magnetic force, as described above, the relationship between the specific gravity of the particles and the specific gravities of the dispersion medium and the transport liquid is not limited particularly.

(Bubble Attaching)

Next, a method for adsorbing bubbles to particles will be described below.

In the exemplary embodiment of the present invention, in the case that bubbles are adsorbed to particles, the bubbles are preferably microbubbles and/or nanobubbles, preferably nanobubbles.

Microbubbles are herein defined as minute bubbles having a diameter of 1 μm or more to 500 μm or less. Apparatuses of a type that performs deposition under reduced pressure, an ultrasonic type and a two-layer circulating type are known as microbubble generators.

In the apparatus of the type that performs deposition under reduced pressure, high-pressure air (gas) is saturatedly dissolved into water (liquid), and the obtained high-pressure water is rapidly subjected to pressure reduction to generate bubbles. In the apparatus of the ultrasonic type, air (gas) is dissolved into water (liquid) under pressure, and the water is subjected to ultrasonic vibration so that the air (gas) dissolved in the water is deposited. Furthermore, in the apparatus of the two-layer circulating type, water (liquid) is passed into a cylindrical vessel in the tangential direction thereof to form a swirling flow, external air (gas) is drawn from the end of the vessel in the axial direction thereof using the negative pressure generated at the axial center of the vessel so that bubbles are generated by the shearing effect of the swirling flow.

On the other hand, nanobubbles are ultrafine bubbles having a diameter of less than 1 μm. It is known that nanobubbles are generated by physically stimulating and crushing micron-size minute bubbles, and it is reported that nanobubbles are present stably for a relatively long time when minus ions are present in the surroundings (for example, Japanese Patent Application Laid-open Publication No. 2005-245817). Hence, when nanobubbles are adsorbed to particles, they are adsorbed to the particles relatively stably. It is therefore conceivable that the particles may be fed without being separated from the nanobubbles even if the particles are fed through the separation path, the discharge paths, etc.

As nanobubble generators, a discharge apparatus, an ultrasonic apparatus and a swirling flow generator (for example, a rotor) are known, and any one of these may be used for the exemplary embodiment of the present invention.

Adsorbing bubbles to particles may be performed at any stage and not limited particularly. However, it is preferable that minute bubbles (preferably nanobubbles) are adsorbed to the particles before the particles are fed to the separation path and that the particles to which the minute bubbles are adsorbed are fed to the separation path.

Moreover, the exemplary embodiment of the present invention is not limited to this configuration, and bubbles may be adsorbed to particles inside the separation path by providing a bubble discharging port on the downstream side of the dispersion liquid introduction port inside the separation path as described in Japanese Patent Application Laid-open Publication No. 2003-251336.

The exemplary embodiment of the present invention will be described below referring to the drawings.

In the following description, the same reference codes represent the same subject matters.

First Embodiment

A first embodiment according to the exemplary embodiment of the present invention will be described below referring to FIG. 1.

Figure 1:
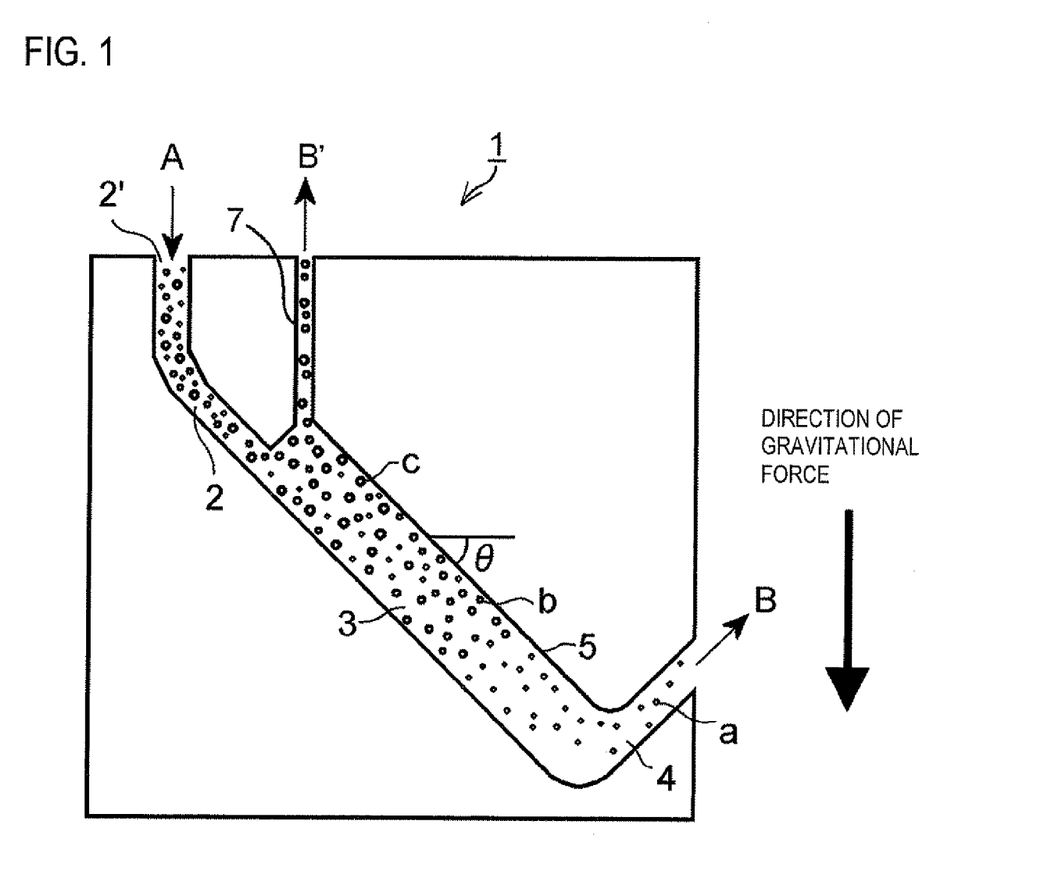
FIG. 1 is a schematic sectional view showing a first embodiment of a separation apparatus usable for the exemplary embodiment of the present invention.

FIG. 1 is a schematic sectional view showing the first embodiment of a separation apparatus usable for the exemplary embodiment of the present invention.

A separation apparatus 1 has a dispersion liquid introduction path 2 that introduces a solution (dispersion liquid) A containing particles, a separation path 3 leading from the dispersion liquid introduction path 2 and the upper face of which is inclined at an angle of θ (45° in FIG. 1) with respect to the horizontal direction, and a discharge path 4, leading from the separation path 3, that discharges the particles having been separated (classified). The horizontal direction is herein defined as the direction intersecting the direction of gravity at a right angle. In the case that the upper face of the path is horizontal, the angle thereof is 0°, and in the case that the upper face of the path is vertical, the angle thereof is 90°.

In FIG. 1, a microchannel having a depth of 500 μm in the depth direction of the sheet of the drawing is formed in a plate-like body shape. Furthermore, the arrow shown in FIG. 1 indicates the direction of gravity.

In the separation apparatus 1 shown in FIG. 1, the dispersion liquid A is fed from a dispersion liquid introduction port 2' provided in the upper portion of the separation apparatus 1 downward in the direction of gravity (downward in the vertical direction) via the dispersion liquid introduction path 2. The method for introducing the dispersion liquid A is not limited particularly, but may be selected appropriately from known methods. It is preferable that pressure-feeding is carried out using a microsyringe, a rotary pump, a screw pump, a centrifugal pump, a piezo pump, etc.

Moreover, although the dispersion liquid A is fed to the dispersion liquid introduction path 2 downward in the direction of gravity (downward in the vertical direction) in FIG. 1, the direction of the feeding is not limited to the downward direction, provided that the dispersion liquid introduction path 2 is provided in the upper portion of the separation apparatus 1. The dispersion liquid introduction path 2 may be provided in a direction horizontal to the upper portion of the separation path 3, or the dispersion liquid introduction path 2 may be extended from the separation path 3 and inclined. In other words, the direction is not limited particularly, provided that the dispersion liquid A is fed from the upper portion of the separation path 3.

The separation apparatus 1 according to the first embodiment will be described below by taking an example in which the dispersion liquid A contains three kinds of particles different in particle diameter: small, medium and large (particles a (small), particles b (medium) and particles c (large)).

In the separation apparatus 1 shown in FIG. 1, when attention is paid to the minute particles a among the particles contained in the dispersion liquid A, since the gravity-direction component velocity (the flow velocity in the direction of gravity) v of the descending velocity (feeding velocity) of the dispersion liquid A is larger than the terminal velocity of the minute particles a, the minute particles a are discharged as a discharge liquid B from the discharge path 4 provided in the lower portion of the separation path 3.

When it is assumed that the total velocity of the dispersion liquid A is V, the gravity-direction component velocity v is given by the following expression.

$$v = V \sin \theta$$

When it is assumed that a single particle is moved through a static fluid by an external force, the terminal velocity is herein defined as the motion velocity of the particle in a state in which the external force exerted to the particle is balanced with the resistance received by the particle from the fluid. In FIG. 1, the external force exerted to the particle is a buoyant force. If the dispersion liquid is fed at a flow velocity larger than the terminal velocity in terms of the component velocity v, the particle descends (is fed). Conversely, if the dispersion liquid is fed at a flow velocity smaller than the terminal velocity, the particle floats.

On the other hand, since the terminal velocity of the large particles c is larger than the component velocity v of the dispersion liquid A, the particles float by virtue of a buoyant force and make contact with the upper face 5 of the separation path 3. Since the flow velocity at the wall face is nearly zero under laminar flow conditions, when the large particles c ascend and make contact with the upper face 5 of the separation path 3, the velocity of the particles floating along the wall face becomes higher than that in the case that the particles float inside the fluid. For this reason, in the apparatus shown in FIG. 1, separation (classification) may be performed rapidly in Comparative with the case in which no inclined separation path is provided, and the efficiency of the separation is improved.

In FIG. 1, the large particles c having floated along the upper face 5 of the separation path 3 are discharged from a second discharge path 7 provided on the upstream side of the separation path 3.

Furthermore, when attention is paid to the particles b having a particle diameter between that of the small particles a and that of the large particles c in FIG. 1, the component velocity v of the dispersion liquid is set slightly smaller than the terminal velocity of the particles b. The particles b gradually float, make contact with the upper face 5 of the separation path 3 on the downstream side (lower side) thereof, float along the upper face 5 of the separation path 3, and are discharged from the second discharge path 7.

Although the component velocity v of the dispersion liquid is set smaller than the terminal velocity of the particles b in FIG. 1, the present embodiment is not limited to this setting. It is also possible to discharge the particles b from the discharge path 4 and to collect them inside the discharge liquid B by setting the component velocity v of the dispersion liquid larger (faster) than the terminal velocity of the particles b.

Moreover, although the particles are separated (classified) into two kinds of particles, that is, the particles discharged from the discharge path 4 and the particles discharged from the second discharge path 7 as shown in FIG. 1, it is also possible to separate (classify) the particles into three or more kinds of particles by providing additional discharge paths in the middle of the separation path 3.

Next, a method for producing the separation apparatus according to the exemplary embodiment of the present invention will be described below.

The separation apparatus according to the exemplary embodiment of the present invention may be produced by carrying out the microfabrication technology on a solid substrate.

Examples of materials to be used as the solid substrate include metal, silicon, Teflon (registered trademark), glass, ceramic and plastic, preferably metal, silicon, Teflon (registered trademark), glass and ceramic in view of heat resistance, pressure resistance, solvent resistance and optical transparency, and particularly preferably glass.

The microfabrication technology for producing such paths is described in, for example, "Micro-reactor—Synthesis Technology for New Age" (published in 2003 by CMC under the editorship of Junichi Yoshida) and "Microfabrication Technology, Applied edition—Application to Photonics, Electronics and Mechatronics" (published in 2003 by NTS, edited by Event Committee of Society of Polymer Science, Japan).

Representative methods include the LIGA technology using X-ray lithography, the high aspect ratio photolithography method using EPON SU-8, the micro electric discharging method (μ-EDM), the silicon high aspect ratio processing method based on Deep RIE, the Hot Emboss processing method, the stereo lithography method, the laser processing method, the ion beam processing method, and the mechanical micro cutting method using a micro-tool made of a hard material such as diamond. These technologies may be used alone or in combination. Preferable microfabrication technologies are the LIGA technology using X-ray lithography, the high aspect ratio photolithography method using EPON SU-8, the micro electric discharging method (μ-EDM) and the mechanical micro cutting method.

The paths for use in the exemplary embodiment of the present invention may be formed by using a pattern as a mold that is formed on a silicon wafer using a photoresist, by pouring resin into the mold and by allowing the resin to cure (the molding method). For the molding method, it is possible to use silicon resin typified by polydimethylsiloxane (PDMS) or its derivatives.

When the separation apparatus according to the exemplary embodiment of the present invention is produced, bonding technology may be used. Ordinary bonding technology is largely divided into solid-phase bonding and liquid-phase bonding. Representative bonding methods being used generally are pressure bonding and diffusion bonding as the solid-phase bonding methods, and welding, eutectic bonding, soldering, adhesion, etc. as the liquid-phase bonding methods.

Furthermore, highly precise bonding methods are desirable in which dimensional accuracy is maintained while minute structures, such as paths, are not damaged owing to heating at high temperature, change in material quality, deformation in material, etc. at the time of bonding. Examples of technologies for the methods include silicon direct bonding, anodic bonding, surface activation bonding, direct bonding using hydrogen bonds, bonding using an HF aqueous solution, Au—Si eutectic bonding, void-free bonding, diffusion bonding, etc.

The separation apparatus according to the exemplary embodiment of the present invention may be formed by laminating pattern members (thin-film pattern members). The thickness of the pattern members is preferably 5 to 50 μm, more preferably 10 to 30 μm. The separation apparatus according to the exemplary embodiment of the present invention may be a separation apparatus in which pattern members having predetermined two-dimensional patterns are laminated. It is preferable that the pattern members are laminated in a state in which the faces thereof are made direct contact with each other and bonded. More specifically, the production method described in Japanese Patent Application Laid-open Publication No. 2006-187684 can be referred to.

In the separation apparatus 1 shown in FIG. 1, the cross-sections of the paths are rectangular. The width of the dispersion liquid introduction path 2 is 500 μm, the width of the separation path 3 is 1,000 μm, and the width of the discharge path 4 is 500 μm. In addition, the depth of these paths is 500 μm.

Furthermore, the length of the dispersion liquid introduction path 2 is 20 mm, the length of the separation path 3 is 50 mm, and the length of the discharge path 4 is 10 mm.

In the first embodiment, particles having a desired particle diameter may be separated (classified) by appropriately selecting the specific gravity and particle diameter of the particles contained in the dispersion liquid, the specific gravity of the dispersion medium also contained in the dispersion liquid, the feeding velocity of the dispersion liquid, etc. Furthermore, as the separation path is longer, the separation (classification) resolution of the separation apparatus becomes higher. However, if the length of the separation path is made longer, the volume required for the separation apparatus increases. It is thus desirable to appropriately select the length depending on the purpose of use.

Second Embodiment

Next, a second embodiment according to the exemplary embodiment of the present invention will be described below referring to FIG. 2.

Figure 2:
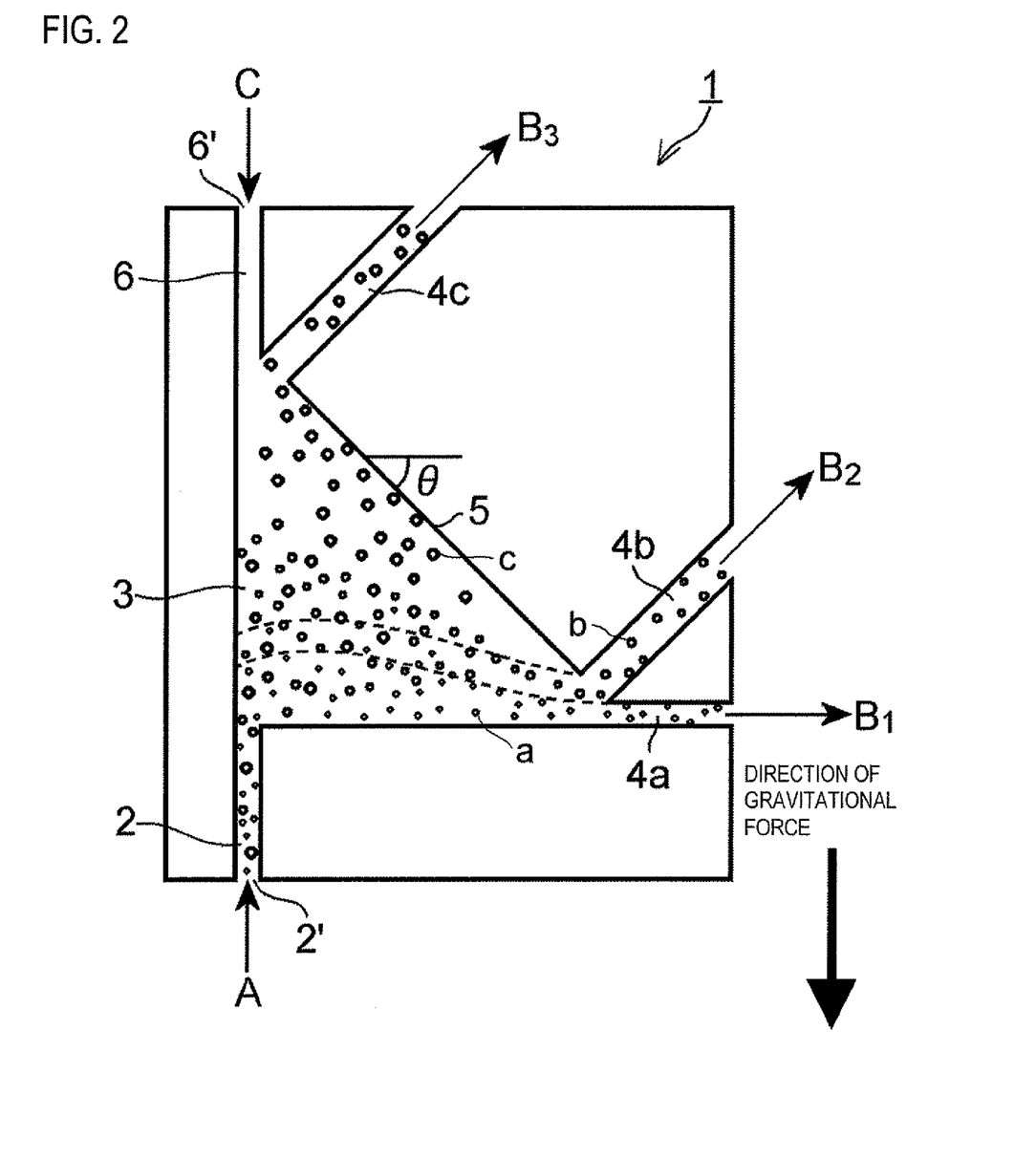
FIG. 2 is a schematic sectional view showing a second embodiment of the separation apparatus usable for the exemplary embodiment of the present invention.

FIG. 2 is a schematic sectional view showing the second embodiment of the separation apparatus usable for the exemplary embodiment of the present invention. In a separation apparatus 1 shown in FIG. 2, a microchannel having a depth of 500 μm in the depth direction of the sheet of the drawing is formed in a plate-like body shape. Furthermore, the arrow shown in FIG. 2 indicates the direction of gravity.

In FIG. 2, the separation apparatus 1 has a dispersion liquid introduction path 2 that introduces a solution (dispersion liquid) A containing particles, a separation path 3 leading from the dispersion liquid introduction path 2 and the upper face of which is inclined at an angle of θ with respect to the horizontal direction, and discharge paths 4a, 4b and 4c, leading from the separation path 3, that discharges the particles having been separated (classified). Furthermore, in the second embodiment, the separation apparatus 1 has a transport liquid introduction path 6.

In the second embodiment, a dispersion liquid introduction port 2' is provided in the lower portion of the separation apparatus 1, and the dispersion liquid A is fed upward relative to the direction of gravity.

In addition, in the second embodiment, the separation path 3 is provided so that its cross-sectional area becomes larger in the advancing direction of the dispersion liquid A.

The configuration in which the cross-sectional area of the separation path becomes larger in the advancing direction of the dispersion liquid has the following advantages. That is to say, if the feeding velocity of the dispersion liquid is low, the dispersion liquid introduction path and/or the separation path may be clogged in some cases. Hence, the feeding velocity of the dispersion liquid is required to be set at a velocity in which no clogging occurs. On the other hand, if the feeding velocity is too high and exceeds the terminal velocity of particles, particle separation may not be carried out sufficiently.

When the cross-sectional area of the separation path becomes larger in the advancing direction of the dispersion liquid, the flow velocity of the dispersion liquid becomes lower as the dispersion liquid is fed to the downstream side. For this reason, it is possible to carry out sufficient separation even if the feeding velocity of the dispersion liquid on the upstream side is increased. Hence, the separation efficiency of the separation apparatus may be improved while clogging is suppressed.

In the second embodiment, the dispersion liquid A is fed from the dispersion liquid introduction port 2' provided in the lower portion of the separation apparatus 1 in a direction opposite to the direction of gravity (upward in the vertical direction) through the dispersion liquid introduction path 2. A transport liquid C is fed from a transport liquid introduction port 6' provided in the upper portion of the separation apparatus 1 through the transport liquid introduction path 6 in the direction of gravity. However, the method for introducing the dispersion liquid A and the transport liquid C is not limited particularly, but may be selected appropriately from known methods as in the case of the first embodiment. Furthermore, the dispersion liquid introduction path 2 and the transport liquid introduction path 6 should only be configured so as to perform liquid feeding from the lower portion and the upper portion of the separation path 3, respectively, and should not be limited to the configuration shown in FIG. 2.

Clogging by the dispersion liquid A may be suppressed by feeding the dispersion liquid A in a direction opposite to the direction of gravity (upward in the vertical direction) through the dispersion liquid introduction path 2 provided in the lower portion of the separation apparatus 1. Furthermore, laminar flow from the upper portion to the lower portion of the separation path 3 occurs by feeding the transport liquid C in the direction of gravity through the transport liquid introduction path 6 provided in the upper portion of the separation apparatus 1.

The dispersion liquid A fed from downward and the transport liquid C fed from upward join together in the separation path 3, an interface is formed therebetween, and laminar flow is generated.

The separation apparatus 1 according to the second embodiment will be described below by taking an example in which the dispersion liquid A contains three kinds of particles different in particle diameter: small, medium and large (particles a (small), particles b (medium) and particles c (large)).

In the separation apparatus 1 shown in FIG. 2, when attention is paid to the minute particles a among the particles contained in the dispersion liquid A, since the floating velocity of the minute particles a is low, most of the minute particles remain in the dispersion liquid A and are discharged from the discharge path 4a, thereby existing in a discharge liquid $B_1$.

On the other hand, the large particles c float upward by virtue of a buoyant force. When the large particles make contact with the upper face 5 of the separation path 3, since the flow velocity of the liquid at the wall face is nearly zero, the large particles float upward rapidly along the upper face and are discharged from the discharge path 4c, thereby being detected in a discharge liquid $B_3$.

Furthermore, the particles b having a particle diameter between that of the small particles a and that of the large particles c float by virtue of a buoyant force and are fed to the discharge path 4b before making contact with the upper face 5 of the separation path 3, thereby being detected in a discharge liquid $B_2$.

Although the three discharge paths in total, i.e., the discharge paths 4a, 4b and 4c, are provided as shown in FIG. 2, the present embodiment is not limited to this configuration, but any desired number of discharge paths may be provided.

Furthermore, particles having a desired particle diameter may be separated (classified) by appropriately changing the position at which the discharge path is provided. Moreover, it is needless to say that the dispersion medium, transport liquid, flow velocity, path widths, path lengths, etc. can be changed as necessary.

FIGS. 3A to 3D are schematic views showing states in which the large and small particles are fed in the separation apparatus according to the second embodiment.

In FIGS. 3A to 3D, an interface 10 (indicated by a solid line in each of FIGS. 3A to 3D) is formed between the dispersion liquid A fed from the lower portion of the separation apparatus 1 and the transport liquid C fed from the upper portion thereof inside the separation path 3. The dispersion liquid A contains the minute particles a and the large particles c.

Figure 3A:
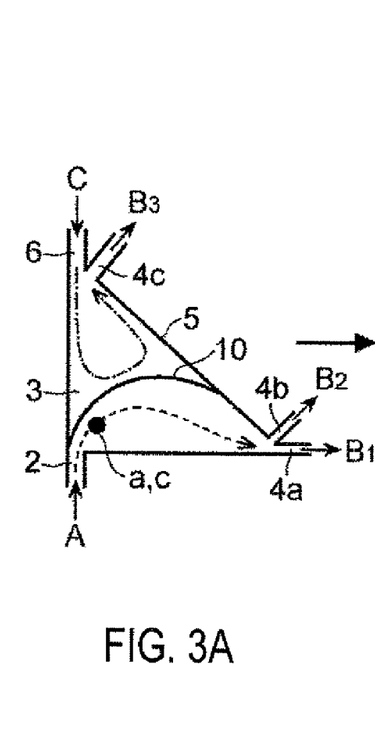
FIGS. 3A to 3D are schematic views showing states in which large and small particles are fed in the separation apparatus according to the second embodiment.
Figure 3B:
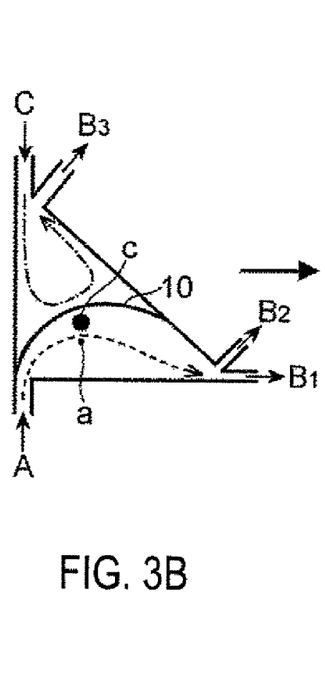
Figure 3C:
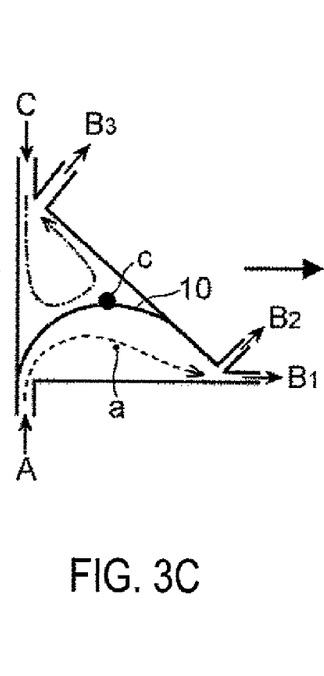
Figure 3D:
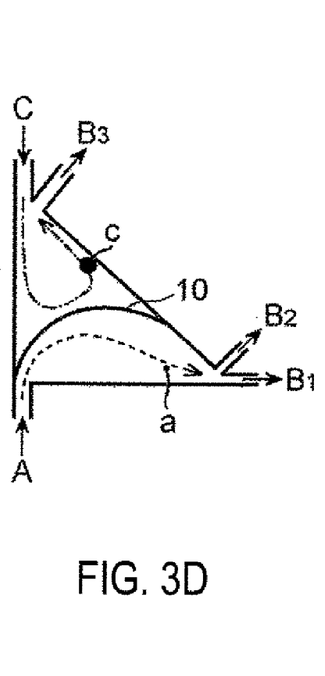

Since the large particles c are significantly influenced by a buoyant force, they gradually float (FIGS. 3B and 3C), make contact with the upper face 5 of the separation path 3, and float upward along the upper face 5 (FIG. 3D). Hence, the large particles c are discharged from the discharge path 4c provided in the upper portion of the separation path 3 as the discharge liquid $B_3$.

On the other hand, the minute particles a are carried along the laminar flow of the dispersion liquid A and discharged as the discharge liquid $B_1$ from the discharge path 4a provided in the lower portion of the separation path 3.

The separation apparatus according to the second embodiment may be produced using materials similar to those used for the separation apparatus according to the first embodiment. In addition, the separation apparatus may also be produced using a method similar to that used for the separation apparatus according to the first embodiment.

Third Embodiment

Figure 4A:
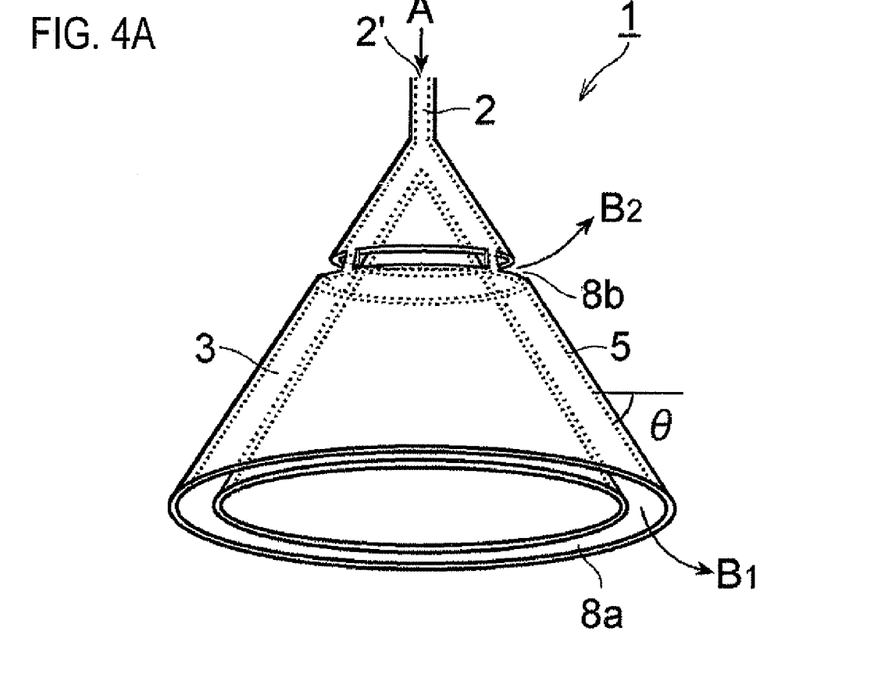
FIGS. 4A and 4B are schematic perspective views showing a third embodiment of the separation apparatus usable for the exemplary embodiment of the present invention.
Figure 4B:
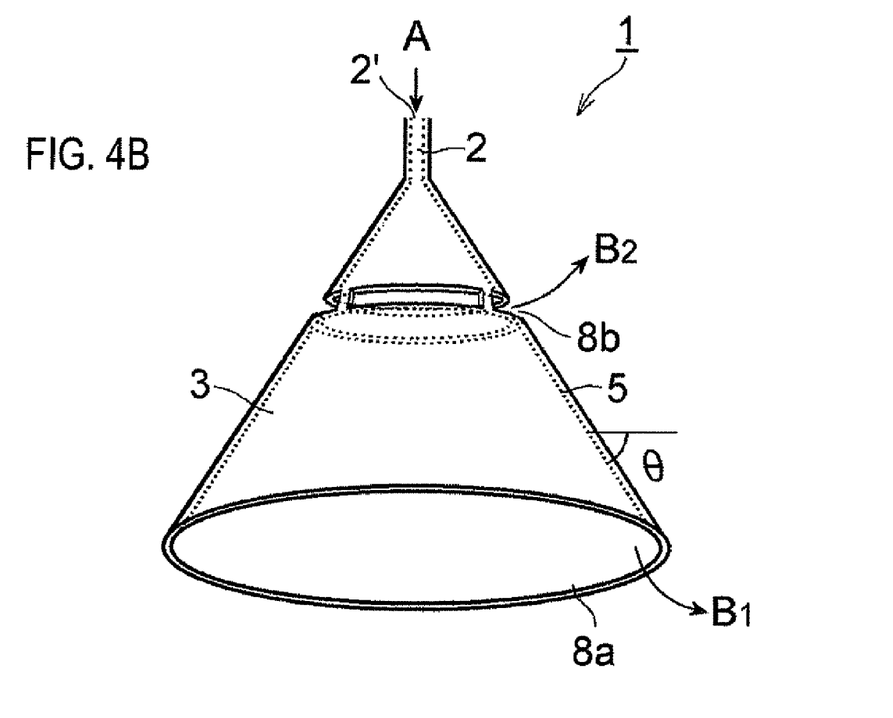

FIGS. 4A and 4B are schematic perspective views showing a third embodiment of the separation apparatus usable for the exemplary embodiment of the present invention. The separation apparatuses 1 shown in FIGS. 4A and 4B are a cone type.

In FIGS. 4A and 4B, the separation apparatus 1 has a dispersion liquid introduction path 2 that introduces a solution (dispersion liquid) A containing particles, a separation path 3 leading from the dispersion liquid introduction path 2 and the upper portion of which is inclined at an angle of θ with respect to the horizontal direction, and discharge paths (not shown), leading from the separation path 3, that discharges the particles having been separated. In FIGS. 4A and 4B, no discharge path is shown, but only pass-through ports 8a and 8b provided in the separation path 3 and leading to the discharge paths are shown.

In the third embodiment, a dispersion liquid introduction port 2' is provided in the upper portion of the separation apparatus 1, and the dispersion liquid A is fed downward to the dispersion liquid introduction path 2 in the direction of gravity (downward in the vertical direction). However, the method for introducing the dispersion liquid A is not limited particularly, but may be selected appropriately as in the case of the first embodiment.

Furthermore, in FIG. 4, although the dispersion liquid A is fed in the direction of gravity (downward in the vertical direction), the direction is not limited to this direction, provided that the dispersion liquid introduction path 2 is provided in the upper portion of the separation apparatus 1. The dispersion liquid introduction path 2 may be provided in the horizontal direction from the upper portion of the separation path 3, and the direction is not limited particularly, provided that the dispersion liquid A is fed from the upper portion of the separation path 3.

Moreover, in the third embodiment, the separation path 3 is provided so that its cross-sectional area becomes larger in the advancing direction of the dispersion liquid A. Since the cross-sectional area of the separation path 3 becomes larger in the advancing direction of the dispersion liquid A, the separation (classification) efficiency of the separation apparatus may be improved while clogging is suppressed as described above.

The thicknesses of the separation path 3 may be made constant as shown in FIG. 4A, or the separation path 3 may be formed into a conical shape as shown in FIG. 4B. The increment in the cross-sectional area of the separation path 3 in the advancing direction of the dispersion liquid A shown in FIG. 4B is larger than that shown in FIG. 4A.

In the third embodiment, since the feeding velocity (descending velocity) of the dispersion liquid A is larger than the terminal velocity of the minute particles a among the particles contained in the dispersion liquid A, the minute particles are discharged from the pass-through port 8a provided in the lower portion of the separation path 3 to one of the discharge paths (not shown) as the discharge liquid $B_1$.

On the other hand, since the feeding velocity (descending velocity) of the dispersion liquid A is smaller than the terminal velocity of the large particles among the particles contained in the dispersion liquid A, the large particles float by virtue of a buoyant force. When the large particles make contact with the upper face 5 of the separation path 3, the large particles float along the wall face thereof and are discharged from the pass-through port 8b provided in the upper portion of the separation path 3 to the other discharge path (not shown) as the discharge liquid $B_2$.

Since the paths of the separation apparatus according to the exemplary embodiment of the present invention have a three-dimensional shape, it is preferable that the separation apparatus is formed by laminating pattern members (thin-film pattern members). The thickness of the pattern members is preferably 5 to 50 μm, more preferably 10 to 30 μm.

It is preferable that the separation apparatus according to the exemplary embodiment of the present invention is a separation apparatus in which pattern members having predetermined two-dimensional patterns are laminated, and it is more preferable that the pattern members are laminated in a state in which the faces thereof are made direct contact with each other and bonded.

The separation apparatus is formed by laminating multiple pattern members corresponding to the respective horizontal cross-sectional shapes of the separation apparatus. This method is thus preferable since the separation apparatus may be formed easily.

As a preferable method for producing the separation apparatus according to the exemplary embodiment of the present invention, it is possible to give an example characterized in that the method comprises (i) the step of forming multiple pattern members corresponding to the respective cross-sectional shapes of a target separation apparatus on a first substrate (the step of producing a donor substrate) and (ii) the step of transferring the multiple pattern members formed on the first substrate to a second substrate by repeating bonding and separation between the first substrate on which the multiple pattern members are formed and the second substrate (the step of bonding). For example, the production method described in Japanese Patent Application Laid-open Publication No. 2006-187684 can be referred to.

The method for producing the separation apparatus according to the exemplary embodiment of the present invention will be described below in more detail.

(Step of Producing Donor Substrate)

In the exemplary embodiment of the present invention, it is preferable that the donor substrate is produced using the electroforming method. The donor substrate is herein defined as a substrate on which multiple pattern members corresponding to the respective cross-sectional shapes of the target separation apparatus are formed on the first substrate. It is preferable that the first substrate is made of metal, ceramic or silicon, and metal such as stainless steel may be used favorably.

First, the first substrate is prepared, a thick-film photoresist is applied onto the first substrate, the photoresist is exposed via a photomask corresponding to the respective cross-sectional shapes of the separation apparatus to be produced, and the photoresist is developed to form a positive-negative inverted resist pattern having the respective cross-sectional shapes. Next, the substrate having this resist pattern is dipped in a plating bath to allow, for example, nickel plating to grow on the surface of the first substrate (metal substrate) not covered with the photoresist. It is preferable that the pattern members are formed of copper or nickel using the electroforming method.

Next, the resist pattern is removed, whereby the pattern members corresponding to the respective cross-sectional shapes of the separation apparatus are formed on the first substrate.

(Step of Bonding)

The step of bonding is defined as a step of transferring the multiple pattern members formed on the first substrate (donor substrate) to the second substrate (target substrate) by repeating bonding and separation between the first substrate on which the multiple pattern members are formed and the second substrate. It is preferable that the bonding is carried out using room-temperature bonding or surface activation bonding.

FIGS. 5A to 5F are views showing the production steps of an embodiment of a method for producing a separation apparatus that may be usable for the third embodiment.

Figure 5A:
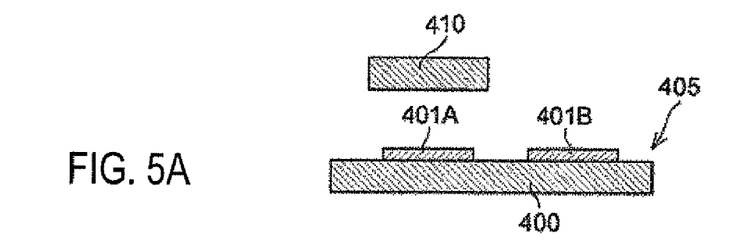
FIGS. 5A to 5F are views showing production steps of an exemplary embodiment of a method for producing the separation apparatus that may be usable for the third embodiment.

As shown in FIG. 5A, the multiple pattern members (401) corresponding to the respective cross-sectional shapes of the target separation apparatus have already been formed on the metal substrate 400 (first substrate) serving as the donor substrate 405. The donor substrate 405 is placed on a lower stage (not shown) inside a vacuum chamber, and the target substrate 410 is placed on an upper stage (not shown) inside the vacuum chamber. Then, the vacuum chamber is evacuated to a high vacuum state or an ultra-high vacuum state. Next, the lower stage is moved relatively with respect to the upper stage so that the first-layer pattern member 401A of the donor substrate 405 is positioned just under the target substrate 410. Next, an argon atom beam is irradiated to the surface of the target substrate 410 and the surface of the first-layer pattern member 401A to clean the surfaces.

Figure 5B:
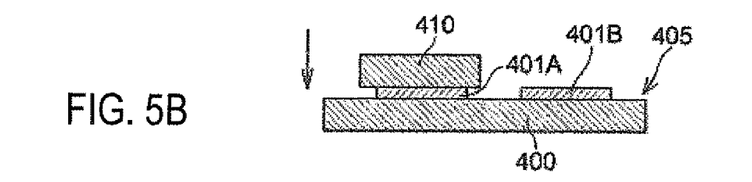

Next, as shown in FIG. 5B, the upper stage is lowered to press the target substrate 410 to the donor substrate 405 with a predetermined loading force (for example, 10 kgf/cm$^2$) for a predetermined time (for example, 5 minutes), whereby the target substrate 410 is bonded to the first-layer pattern member 401A at room temperature (surface activation bonding). In the exemplary embodiment of the present invention, the pattern members 401A, 401B, . . . are laminated in this order.

Figure 5C:
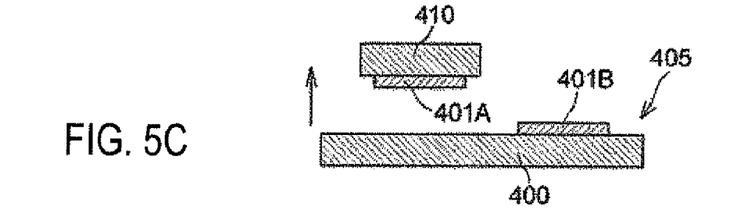

Next, as shown in FIG. 5C, the upper stage is raised so that the target substrate is separated from the donor substrate, whereby the first-layer pattern member 401A is peeled off from the metal substrate (first substrate) 400 and transferred to the target substrate 410. This transfer occurs because the adhesion strength between the first-layer pattern member 401A and the target substrate 410 is larger than the adhesion strength between the first-layer pattern member 401A and the metal substrate 400 (first substrate).

Figure 5D:
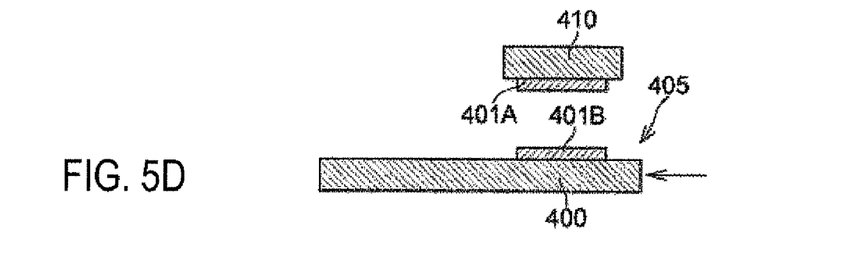

Next, as shown in FIG. 5D, the lower stage is moved so that the second-layer pattern member 401B on the donor substrate 405 is positioned just under the target substrate 410. Then, the surface of the first-layer pattern member 401A (the surface which made contact with the metal substrate 400) transferred to the target substrate 410 and the surface of the second-layer pattern member 401B are cleaned as described above.

Figure 5E:
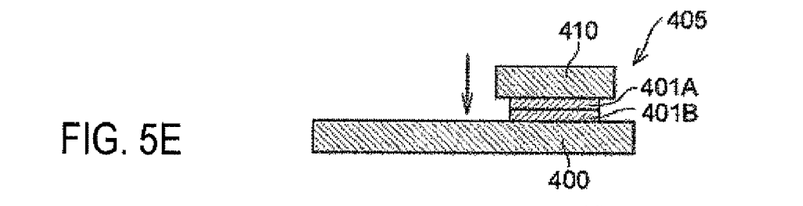
Figure 5F:
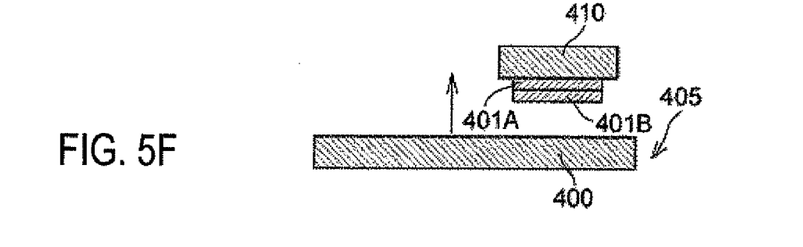

Next, as shown in FIG. 5E, the upper stage is lowered so that the first-layer pattern member 401A is bonded to the second-layer pattern member 401B. Then, as shown in FIG. 5F, the upper stage is raised, whereby the second-layer pattern member 401B is peeled off from the metal substrate (first substrate) 400 and transferred to the target substrate 410.

The other pattern members are also repeatedly subjected to positioning, bonding and separation between the donor substrate 405 and the target substrate 410 in a similar way. As a result, the multiple pattern members corresponding to the respective cross-sectional shapes of the separation apparatus are transferred onto the target substrate. The laminated body transferred onto the target substrate 410 is detached from the upper stage, and the target substrate 410 is removed, whereby the separation apparatus is obtained.

Although the donor substrate is produced using the electroforming method in the above-mentioned embodiment, the donor substrate may also be produced using the semiconductor process. For example, a substrate made of a Si wafer is prepared, and a mold releasing layer made of polyimide is formed on this substrate using the spin coating method. An Al thin film serving as a component material of the separation apparatus is formed on the surface of this mold releasing layer using the sputtering method. The Al thin film is patterned using the photolithography method, whereby the donor substrate may be produced.

Although the exemplary embodiment of the present invention will be described below in more detail using an example, the exemplary embodiment of the present invention is not limited at all to the example described below.

Figures 6A, 6B:
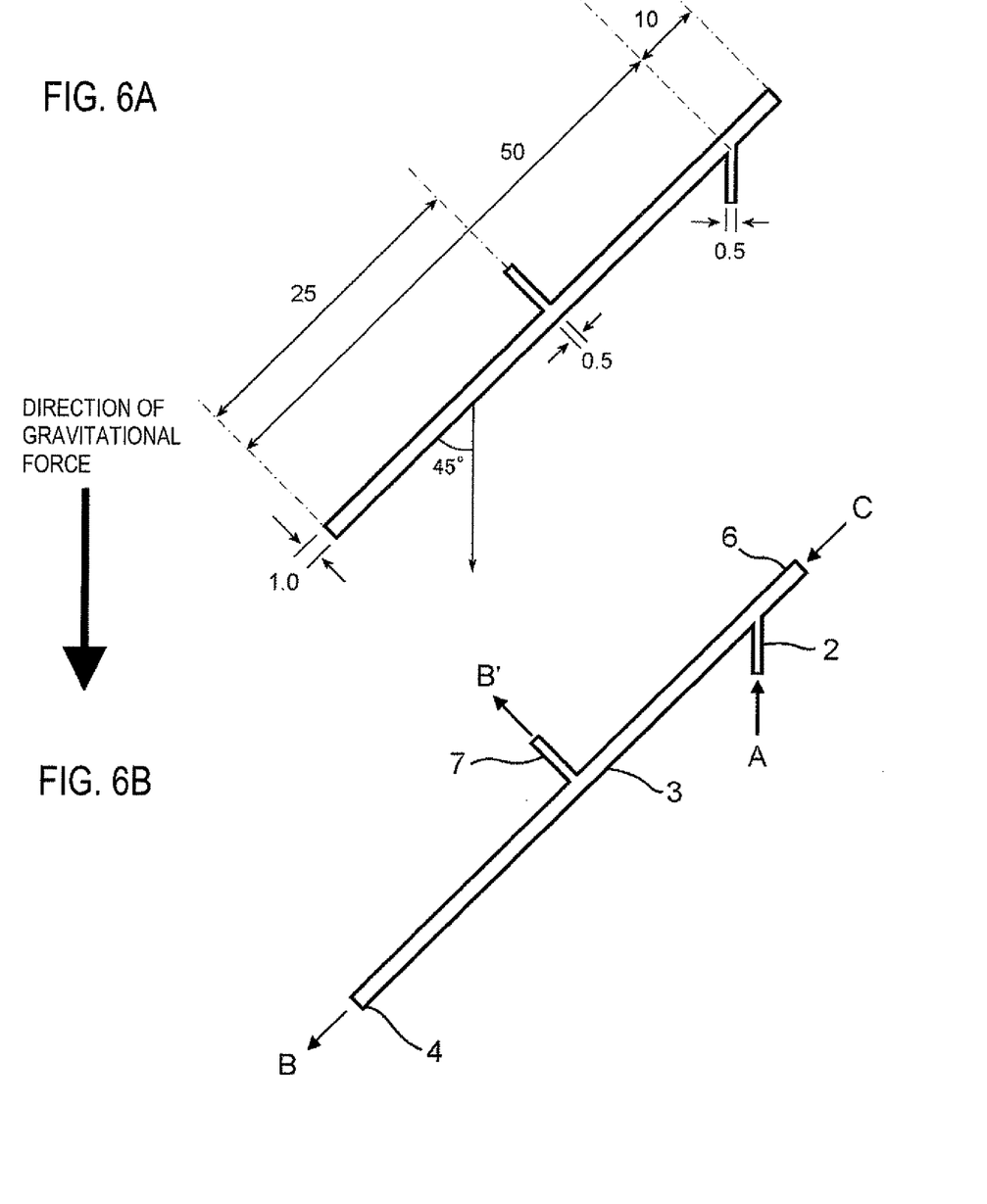
FIGS. 6A and 6B are schematic views showing a separation apparatus used in Example 1.

In the example, classification is performed using the separation apparatus 1 shown in FIGS. 6A and 6B.

In FIGS. 6A and 6B, the paths (the dispersion liquid introduction path, the transport liquid introduction path, the separation path and the discharge paths) of the separation apparatus are all provided in a plate-like body having a depth of 0.5 mm.

The width of the dispersion liquid introduction path 2 is 0.5 mm. In addition, the widths of the separation path 3 and the discharge path 4 are 1 mm. The overall length of the separation path 3 is 50 mm, and the end portion thereof serves as the discharge path 4 from which a discharge liquid B containing minutes particles is discharged. Furthermore, the second discharge path 7 that discharges a discharge liquid B' containing large particles is provided in the middle of the separation path 3. The width of the second discharge path 7 is 0.5 mm. Moreover, the separation apparatus was installed so that the upper face of the separation path 3 is inclined at an angle of 45° with respect to the horizontal direction.

A microsyringe is used to introduce the dispersion liquid A and the transport liquid C.

In addition, in FIGS. 6A and 6B, the direction of gravity is indicated by a down-pointing arrow.

Figure 7A:
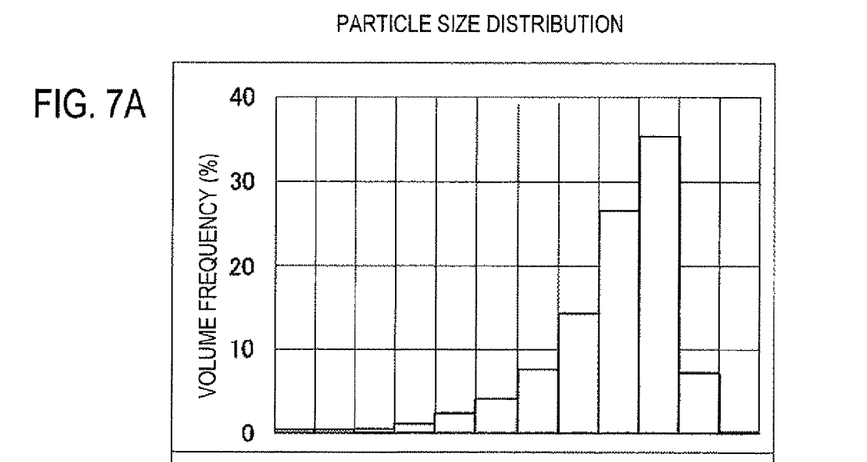
FIG. 7A shows the particle size distribution of the particles in the dispersion liquid A in Example 1.

The dispersion liquid is 10 volume percent of an aqueous dispersion liquid containing polyolefin particles (produced by Nippon Seiro Co., Ltd.) having a volume-weighted mean diameter of approximately 15 μm (obtained by pulverizing paraffin wax having a melting point of 85° C. using a Gaulin mixer). The specific gravity of the polyolefin particles is 0.90 times the specific gravity of water. FIG. 7A is a diagram showing the particle size distribution of the particles in this dispersion liquid.

Figure 7B:
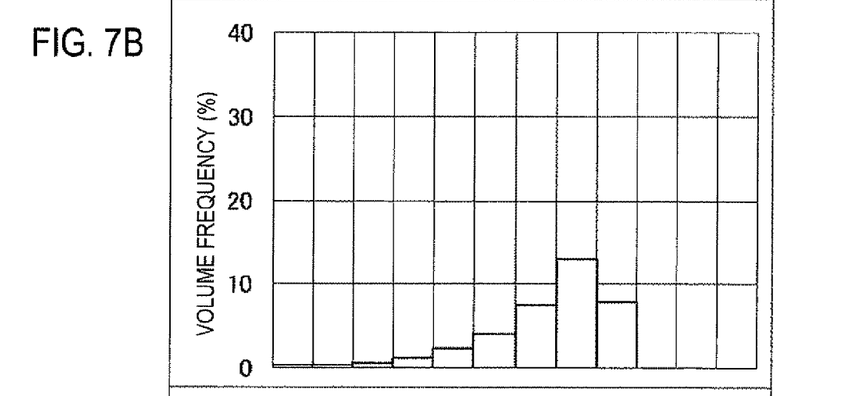
FIGS. 7B and 7C show the particle size distribution of the particles in the discharge liquids (B and B') discharged from the discharge path 4 and the second discharge path 7 of the separation apparatus in Example 1.
Figure 7C:
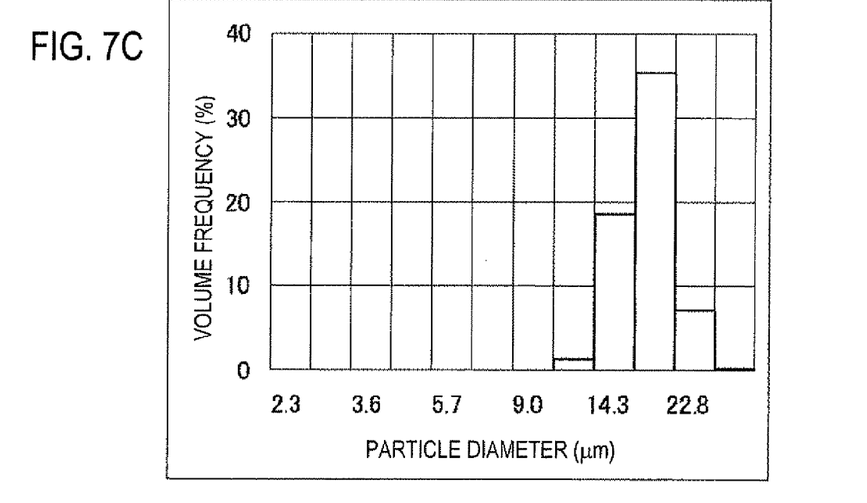

Both the dispersion liquid and the transport liquid are fed at 1 ml/h, and samples are collected from the discharge path 4 (fine powder outlet) and the second discharge path 7 (coarse powder outlet). FIGS. 7B and 7C show the measurement results of the particle size distribution of the particles in these samples.

With this separation method, it was possible to remove particles having a diameter of 18 μm or more.

COMPARATIVE EXAMPLE 1

Figure 8A:
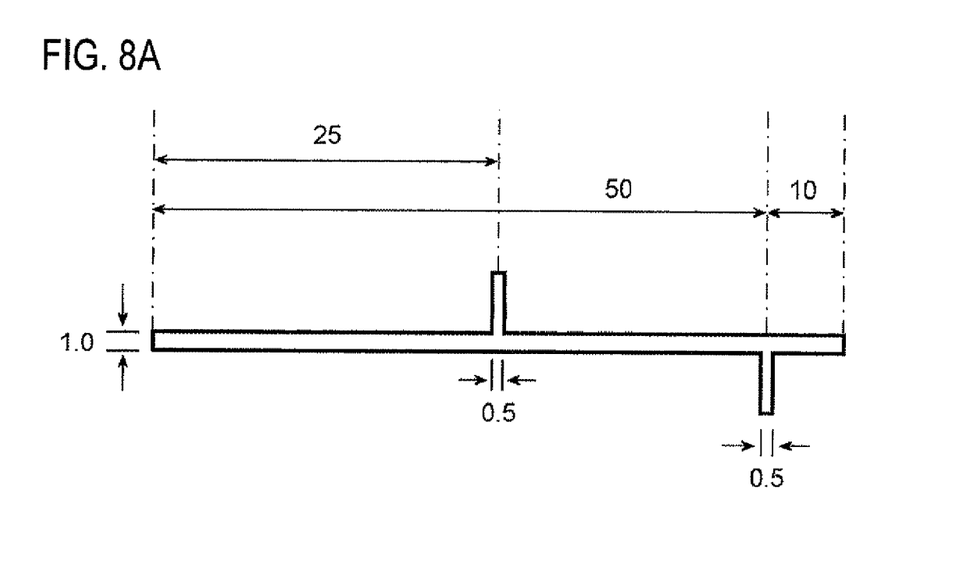
FIGS. 8A and 8B are schematic views showing a separation apparatus used in Comparative example 1.
Figure 8B:
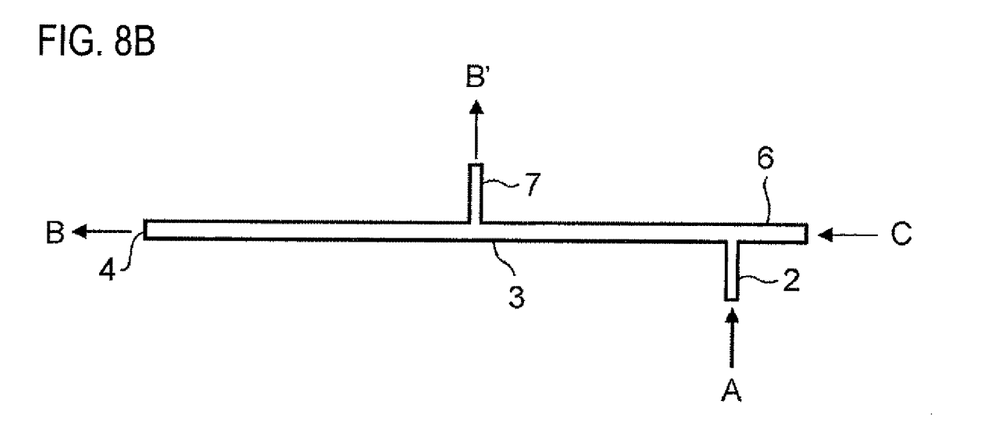
Figure 9A:
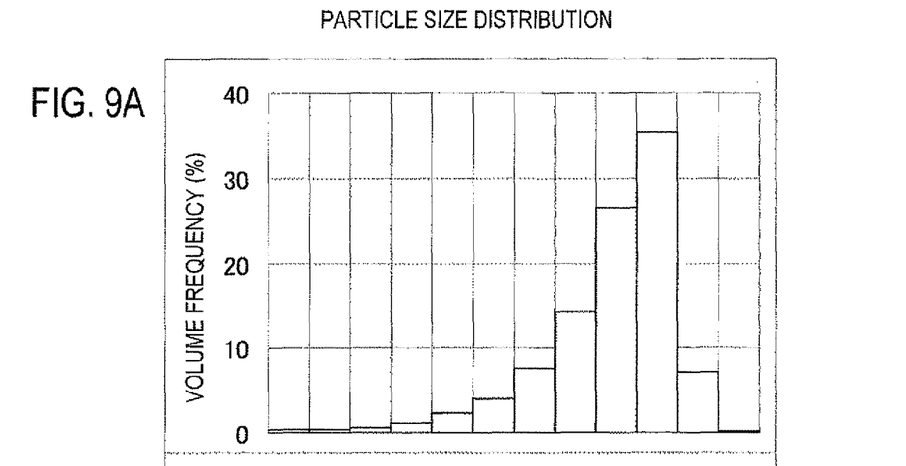
FIG. 9A shows the particle size distribution of the particles in the dispersion liquid A in Comparative example 1.
Figure 9B:
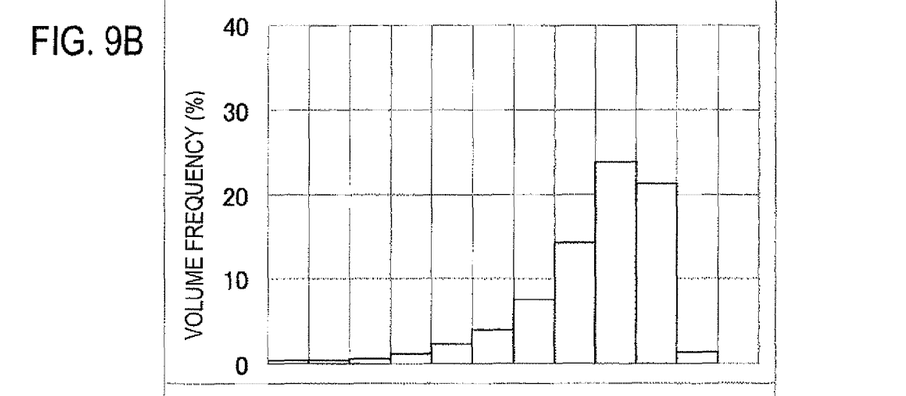
FIGS. 9B and 9C show the particle size distribution of the particles in the discharge liquids (B and B') discharged from the discharge path 4 and the second discharge path 7 of the separation apparatus in Comparative example 1.
Figure 9C:
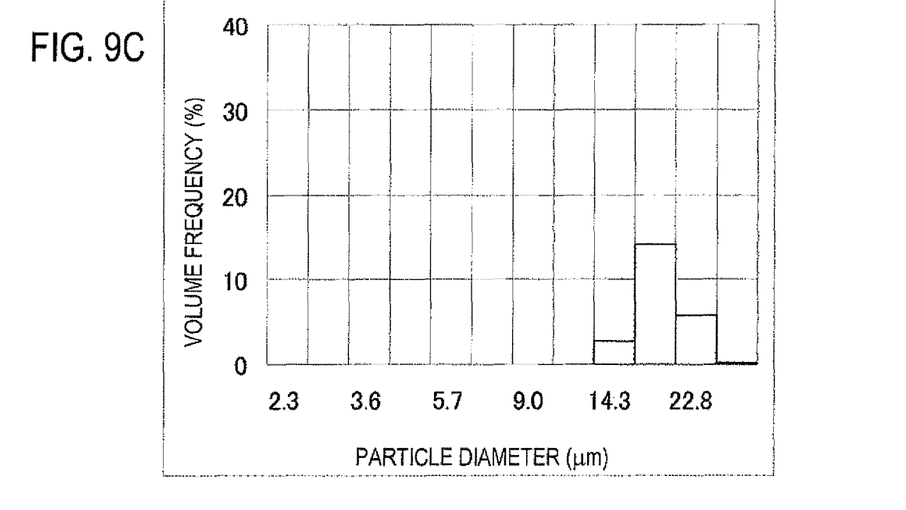

The separation apparatus shown in FIGS. 8A and 8B is the separation (classification) apparatus shown in FIGS. 6A and 6B. The separation apparatus is installed so that the upper face of its classification path is aligned in parallel with the horizontal direction. Samples are collected by using the separation apparatus shown in FIGS. 8A and 8B and a dispersion liquid similar to that in the example and by performing liquid feeding at a feeding velocity similar to that in the example. FIG. 9A is a diagram showing the particle size distribution of the particles in this dispersion liquid. FIGS. 9B and 9C show the measurement results of the particle size distribution of the particles in these samples.

With this separation method, particles having a diameter of 22 μm are detected at the fine powder outlet, whereby sufficient separation capability was not obtained.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention defined by the following claims and their equivalents.

What is claimed is:

1. A separation apparatus, comprising:
   a separation path that has a bottom wall and an upper wall inclined with respect to a direction of gravity and separates particles contained in a dispersion liquid;
   a dispersion liquid introduction path that introduces the dispersion liquid into the separation path; and
   a discharge path that discharges particles separated by the separation path from the separation path,
   wherein the seperation path has a circle-equivalent diameter and wherein the circle-equivalent diameter of the separation path is about 10 μm or more and about 10 mm or less.

2. The separation apparatus according to claim 1, wherein the separation path is disposed so that the dispersion liquid flows from upward to downward with respect to the direction of gravity.

3. The separation apparatus according to claim 1, further comprising:
   a transport liquid introduction path that introduces a transport liquid transporting the dispersion liquid into the separation path.

4. The separation apparatus according to claim 3, wherein the transport liquid introduction path is disposed so that the transport liquid flows from upward to downward with respect to the direction of gravity.

5. The separation apparatus according to claim 1, wherein the separation path has a cross-sectional area that becomes larger in a flowing direction of the dispersion liquid.

6. The separation apparatus according to claim 1, wherein the separation path has a cone shape.

7. The separation apparatus according to claim 1, wherein a dispersion medium of the dispersion liquid has a specific gravity that is larger than a specific gravity of the particles.

8. The separation apparatus according to claim 1, wherein the separation path further contains an applying device that applies an electric field or a magnetic field into the dispersion liquid.

9. A separation method comprising:
   introducing a dispersion liquid containing particles into a separation path that has a bottom wall and an upper wall inclined with respect to a direction of gravity through a dispersion liquid introduction path;
   separating the particles by passing the dispersion liquid through the separation path; and
   discharging particles separated by the separation path from the separation path through a discharge path,
   wherein a circle-equivalent diameter of the separation path is about 10 μm or more and about 10 mm or less.

10. The separation method according to claim 9, wherein the dispersion liquid flows from upward to downward with respect to the direction of gravity in the separating step.

11. The separation method according to claim 9, further comprising:
    introducing a transport liquid into a transport liquid introduction path, the transport liquid transporting the dispersion liquid,
    wherein the transport liquid introducing step flows the transport liquid from upward to downward with respect to the direction of gravity.

12. The separation method according to claim 9, wherein the separation path has a cross-sectional area that becomes larger in a flowing direction of the dispersion liquid.

13. The separation method according to claim 9, wherein the separation path has a cone shape.

14. The separation method according to claim 9, wherein a dispersion medium of the dispersion liquid has a specific gravity that is larger than a specific gravity of the particles.

15. The separation method according to claim 9, further comprising:
    applying an electric field or a magnetic field into the dispersion liquid.

16. The separation method according to claim 9, further comprising:
    adsorbing microbubbles or nanobubbles to the particles.

17. The separation apparatus according to claim 1, wherein the upper wall is not perpendicular to the direction of gravity.

* * * * *